United States Patent
Wild et al.

(10) Patent No.: US 7,469,586 B2
(45) Date of Patent: Dec. 30, 2008

(54) SENSOR UNIT HAVING A CONNECTION CABLE

(75) Inventors: Bernhard Wild, Markgroeningen (DE); Rainer Maier, Tamm (DE); Thomas Wahl, Pforzheim (DE); Juergen Wilde, Fellbach (DE); Gregor Jaehnig, Muehlacker (DE); Peter Dettling, Waiblingen (DE); Stefan Heinzelmann, Kernen (DE); Bernd Rattay, Stuttgart (DE); Bastian Buchholz, Stuttgart (DE); Juergen Moratz, Neuhausen A.D.F. (DE)

(73) Assignee: Robert Bosch GmbH, Stuttgart (DE)

( * ) Notice: Subject to any disclaimer, the term of this patent is extended or adjusted under 35 U.S.C. 154(b) by 170 days.

(21) Appl. No.: 11/449,192

(22) Filed: Jun. 7, 2006

(65) Prior Publication Data

US 2007/0000304 A1      Jan. 4, 2007

(30) Foreign Application Priority Data

Jun. 7, 2005  (DE) ...................... 10 2005 026 068

(51) Int. Cl.
*G01D 11/24* (2006.01)
(52) U.S. Cl. ........................ 73/431; 73/866.5
(58) Field of Classification Search ................ 73/431, 73/866.5, 31.05
See application file for complete search history.

(56) References Cited

U.S. PATENT DOCUMENTS

| | | | | |
|---|---|---|---|---|
| 1,605,648 A | * | 11/1926 | Cooke | 95/79 |
| 1,783,802 A | * | 12/1930 | Lagerblade | 428/598 |
| 2,736,872 A | * | 2/1956 | Heath et al. | 439/581 |
| 3,041,575 A | * | 6/1962 | Schneider | 439/393 |
| 3,124,437 A | * | 3/1964 | Lagarias | 95/75 |
| 3,343,178 A | * | 9/1967 | Palmer | 210/360.2 |
| 3,701,006 A | * | 10/1972 | Volkel et al. | 324/442 |
| 3,946,198 A | * | 3/1976 | Foote | 219/497 |
| 4,001,758 A | * | 1/1977 | Esper et al. | 338/34 |
| 4,345,370 A | * | 8/1982 | Cartier et al. | 29/828 |
| 4,764,343 A | * | 8/1988 | Nyberg | 422/83 |
| 4,786,397 A | * | 11/1988 | Barbieri et al. | 204/427 |
| 4,856,868 A | * | 8/1989 | France et al. | 385/109 |
| 4,930,856 A | * | 6/1990 | Pelta | 385/87 |
| 5,153,931 A | * | 10/1992 | Buchanan et al. | 385/12 |
| 5,173,264 A | * | 12/1992 | Zaromb et al. | 422/88 |
| 6,233,384 B1 | * | 5/2001 | Sowell et al. | 385/107 |
| 6,577,795 B2 | * | 6/2003 | Tuminaro | 385/102 |

(Continued)

FOREIGN PATENT DOCUMENTS

CH         689741 A5  *  9/1999

(Continued)

*Primary Examiner*—David A. Rogers
(74) *Attorney, Agent, or Firm*—Kenyon & Kenyon LLP

(57) ABSTRACT

A sensor unit for determining a physical sensor parameter of a measuring gas, in particular an oxygen concentration in an exhaust gas of an internal combustion engine is provided, which includes a sensor housing and at least one connection cable having an electrically insulating cable sheathing, for the transmission of energy and/or the sensor parameter, the sensor housing having at least one cable opening for the connection cable and at least one sealing element for sheathing and sealing the connection cable, the cable having better sealing than the related art and/or the ability to resist higher temperature loading. According to the invention, this is achieved by at least partially forming the sealing element as tube.

15 Claims, 2 Drawing Sheets

U.S. PATENT DOCUMENTS

| | | | |
|---|---|---|---|
| 6,761,752 B2 * | 7/2004 | Fissan et al. | 95/74 |
| 6,925,852 B2 * | 8/2005 | Susko | 73/23.2 |
| 6,955,075 B2 * | 10/2005 | Carlson et al. | 73/28.02 |
| 7,062,975 B2 * | 6/2006 | Schmid et al. | 73/756 |
| 7,243,560 B2 * | 7/2007 | Coyle et al. | 73/863.22 |
| 2005/0105079 A1 * | 5/2005 | Pletcher et al. | 356/72 |

FOREIGN PATENT DOCUMENTS

| | | |
|---|---|---|
| DE | 41 26 378 | 4/1992 |
| DE | 195 42 650 | 5/1997 |
| EP | 525216 A1 * | 2/1993 |
| JP | 57115693 A * | 7/1982 |
| JP | 06117892 A * | 4/1994 |

* cited by examiner

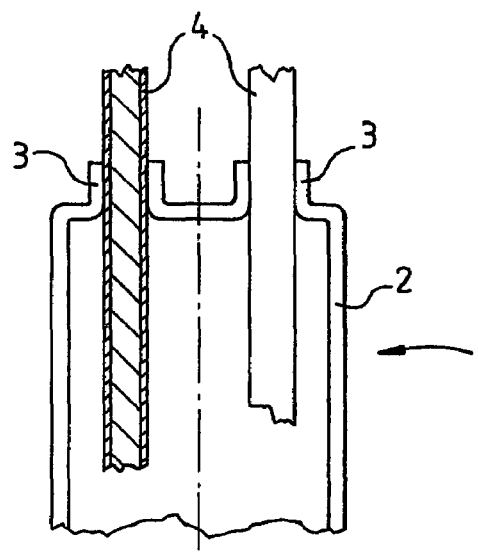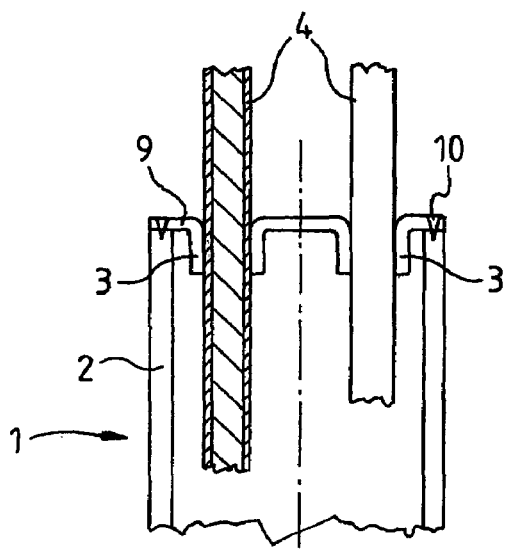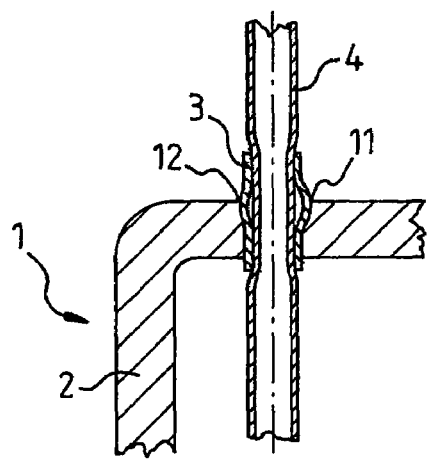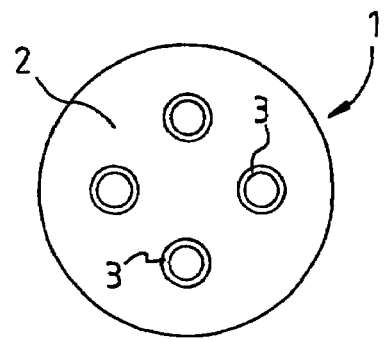

SENSOR UNIT HAVING A CONNECTION CABLE

FIELD OF THE INVENTION

The present invention relates to a sensor unit for determining a physical sensor parameter of a measuring gas, in particular an oxygen concentration in an exhaust gas of an internal combustion engine.

BACKGROUND INFORMATION

Gas sensors, in particular lambda sensors, generally have a housing through which the electrical connection cables for the sensor element must be fed on the front-side, for instance. The sensor element is contacted by the connection cables inside the housing. The gas sensors for determining the exhaust-gas composition in motor vehicles are installed in the exhaust pipe and thus are exposed to the environmental influences prevailing there. The sensor element situated inside the housing often must not come into contact with detrimental environmental influences such as dirt, oil and/or water. It is therefore necessary to provide sealing of the cable feedthrough both with respect to the housing and the cable insulation.

From German Published Patent Application No. 41 26 378 and also from German Published Patent Application No. 195 42 650, cable feedthroughs are known in which the connection cables are guided through an elastic, plug-type molded part and sealed. The molded part is made of a temperature-resistant material such as PTFE (Teflon) and is enclosed and compressed by a housing sleeve, which forms the housing. According to German Published Patent Application No. 41 26 378, for instance, an O-ring is additionally inserted for sealing between housing sleeve and molded part. The O-ring is made of an elastomer such as Viton and has only limited temperature resistance.

According to German Published Patent Application No. 195 42 650, a plug made of PTFE is provided, which is to ensure sealing not only with respect to the cables but with respect to the housing as well. A support ring is inserted in an annular groove of the PTFE plug for this purpose.

However, lately lambda sensors of the exhaust tract are being moved closer and closer to the engine in vehicle applications, so that the temperature loading of corresponding sensors has increased steadily. It has become apparent, however, that the cable feedthroughs according to the related art are unable to tolerate the temperature loading in very close proximity to the engine in the long term.

SUMMARY OF THE INVENTION

In contrast, it is the object of the present invention to provide a sensor unit for determining a physical sensor parameter of a measuring gas, which has a sensor housing and at least one connection cable, provided with an electrically insulating cable sheathing, for the transmission of energy and/or the sensor parameter; the sensor housing has at least one cable opening for the connection cable and at least one sealing element for sheathing and sealing the connection cable, the cable providing better sealing than in the related art and/or having the ability to withstand the increased temperature loading.

The measures indicated make possible advantageous embodiments and further developments of the present invention.

Accordingly, a sensor unit of the present invention is characterized by the sealing element being at least partially in the form of a tube. With the aid of this measure, a connection cable is able to be individually sheathed or sealed by the tube. This improves the sealing, which is reflected in higher temperature resistance, in particular.

Moreover, a tube has a relatively large surface area per volume unit, which may lead to even greater temperature radiation in special application cases, so that the temperature resistance is improved further.

In an advantageous manner, a wall thickness of the tube is several times smaller than the outer diameter of the connection cable. This allows the temperature radiation of the tube or the sealing element to be increased further, which further increases the temperature resistance and thus the durability in long-term loading of the seal.

Furthermore, according to the present invention, in particular according to the mentioned variant, it has become apparent that the inside or the gas-filled interior chamber of the sensor unit may have a particularly large design. This additionally increases the temperature resistance of the sensor unit according to the present invention.

In an advantageous manner, the wall thickness of the tube is essentially between 0.01 mm and 1.0 mm, preferably between 0.05 and 0.6 mm. Experience has shown that this allows especially advantageous sealing elements or tubes to be produced.

In an advantageous specific embodiment of the present invention, the outer diameter of the tube is essentially between 0.01 and 6.0 mm. This measure ensures that standard cables are able to be used in an elegant manner, which constitutes an economical implementation of the present invention.

Different high-temperature materials such as metals, ceramics or the like may be used as material for the sealing element or tube. Preferably used are tubes that are made of a permanently deformable material. Metals, in particular heat-resistant and/or non-corroding steels or tin alloys, are used in an advantageous manner, such as 1.4301, 1.4845, 1.4833, 1.4950, 2.4851, 2.4816, 2.4633 etc.

In an advantageous specific embodiment of the present invention, at least in the installed state, an inside diameter of the tube is smaller than the outer diameter of the connection cable in the non-installed state. This measure allows an especially optimal sealing of the connection cable from the tube or the housing to be achieved. For instance, the electrically insulating cable sheathing, which advantageously is designed to be at least in part elastically deformable, is at least partially molded or compressed in the installed state, so that advantageous sealing is realized.

To implement the sealing with the aid of the tube, for example, the tube may be crimped, compressed etc. during the installation procedure, so that the sealing of the connection cable is realized in an advantageous manner. Tamping of the tube situated around the connection cable is preferably provided. This measure ensures an especially optimal sealing of the connection cable from the tube. The tamping is also particularly advantageous in very high temperature loading of the tube.

In a special further refinement of the present invention, the tube has at least one flange for placement on the sensor housing. The advantageous flange allows especially simple sealing and/or affixation on the sensor housing. For instance, a relatively large contact surface is realized to affix or seal the flange from the sensor housing. This allows especially optimal, in particular long-lasting sealing.

The sensor housing preferably encloses the tube. Special sealing of the tube(s) with respect to the sensor housing may be omitted when using a correspondingly formed, one-piece sensor housing with tube(s). This reduces the constructive as well as the production expense, which may lead to an especially cost-effective sensor unit. If appropriate, the sensor housing and the tube(s) are produced together in an essentially joint working process, using a deep-drawing method or the like, for example.

In an advantageous variant of the present invention, the tube is able to be produced by flow-drilling methods. The tube may thus be produced in a non-cutting manner, for instance. Moreover, a tube produced in this way achieves savings in material and weight. In addition, it is advantageous that a certain hardening of the material is realized, which allows an especially robust specific embodiment of the tube according to the present invention and thus high durability in long-term loading.

A flow-drilling method within the meaning of the present invention is understood to be a combination of axial force and relatively high rotational speed of a tool, in which localized heat between the workpiece and the tool is generated by friction. The frictional heat and the high surface pressure plasticize the material during production.

As an alternative, the tube may also be produced from extruded profiles or the like, which are cut or sawed off according to the desired length. The tube may also be produced from sheet metal that is milled and welded at the abutting surfaces.

In an advantageous manner, at least one welding point and/or one welding seam is provided for welding the sensor housing to the tube. This variant is to be understood as an alternative to the one-piece sensor housing with tube, in particular. With the aid of the welding method according to the present invention, an integral sealing or joining of the tube to the housing that is especially temperature-resistant may be implemented.

Especially in the variant where the tube has at least one flange, this flange may be welded to the sensor housing in an elegant manner, and thereby integrally sealed.

The diameter of the cable opening of the sensor housing is preferably equal to or smaller than the diameter of the tube. This allows a press fit to be realized, which may also implement a continuous material sealing. The cable opening preferably has an advantageous cutting and/or sealing edge so as to seal the opening from the tube. If appropriate, and in particular in the variants of the invention mentioned last, the tube is fixed in place by a single welding spot only, which effectively minimizes the risk of losing the tube according to the present invention.

In general, an advantageous thermoelastic material may be used as electrically insulating cable sheathing. Thermoelastics according to the present invention are thermoplastic plastics which are essentially made up of a chain molecule and in fact transition to a thermoelastic range in response to heating, but are not sufficiently liquid after melting of the crystalline regions, so that they are generally unable to be processed in a manner that would allow injection molding or extrusion.

In an advantageous manner, the electrically insulating cable sheathing of the connection cable essentially includes polytetrafluorethylene. Polytetrafluorethylene (PTFE/Teflon) has particularly good thermoelastic characteristics and thus ensures an especially high quality of the seal between the connection cable and the tube. In an advantageous manner a relatively thin-walled cable sheathing is realized. Especially when using PTFE as cable sheathing, the cable sheathing is able to assume a doughy state in response to temperature loading; nevertheless, the PTFE material will not flow too heavily but essentially retain its position between the electrical conductor of the connection cable and the tube according to the present invention. This advantageously ensures reliable sealing according to the present invention.

In a special embodiment of the present invention, at least two connection cables are provided and each connection cable is assigned at least one separate sealing element and/or tube. With the aid of this measure, the individual sealing of each connection cable is implemented in an elegant manner. If necessary, each connection cable may be specially adapted in this manner or sealed independently of the other connection cable, which results in an especially high sealing quality. For instance, lambda probes are currently in use, which have two to four connection cables, so that two to four tubes have to be provided according to the present invention.

In an advantageous manner, the tube has an electrically insulting coating on the inside or is provided with an inner electrical insulation element. This advantageously improves the insulation effect of a PTFE sheathing of the electrical conductor, which is designed to be relatively thin in special application cases, or two redundant electrical insulation possibilities are produced. In this way the operating reliability is improved further.

BRIEF DESCRIPTION OF THE DRAWINGS

FIG. 3 shows a schematic section through a third sensor unit according to the present invention.

FIG. 4 shows a schematic section through a fourth sensor unit according to the present invention.

FIG. 5 shows a schematic section through a fifth sensor unit according to the present invention.

FIG. 6 shows a schematic plan view of the sensor unit of the present invention according to FIG. 3 or 5.

DETAILED DESCRIPTION

Figure 1:
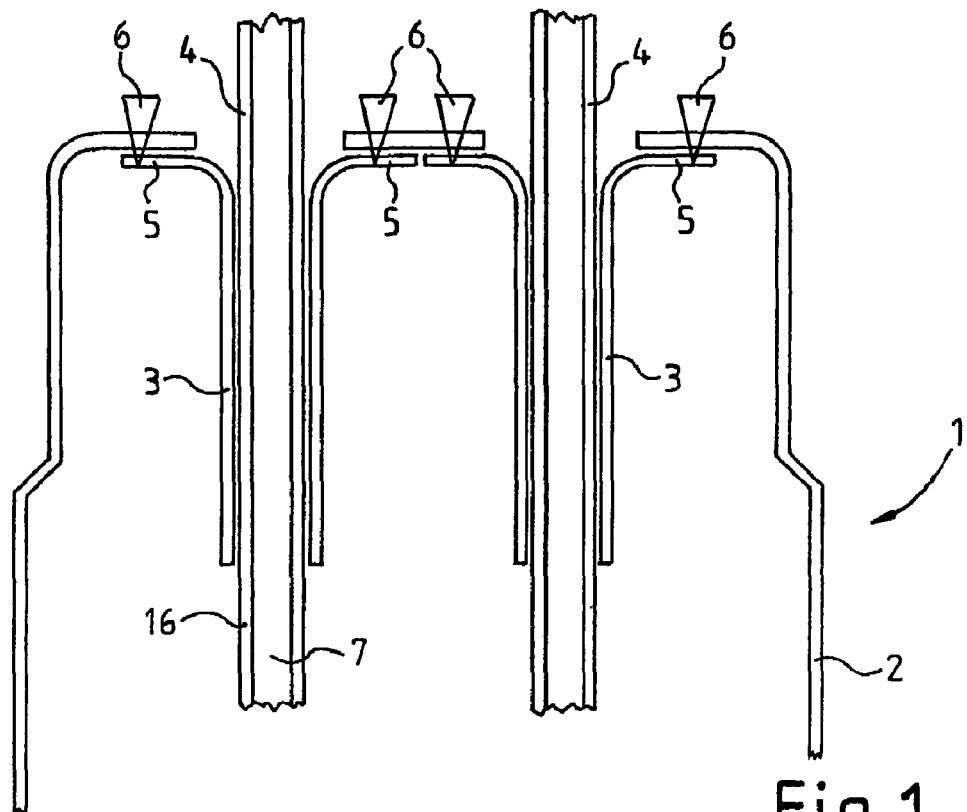
FIG. 1 shows a schematic section through a first sensor unit according to the present invention.

FIG. 1 shows a schematic sectional view of a sensor unit according to the present invention having a housing 1. Housing 1 includes a so-called protective sleeve 2, which is welded to tubes 3 or their flange 5 at the end face. A welding seam 6 is schematically illustrated as triangle in each case.

Using a contact welding method or the like, a correspondingly continuous and thus completely form-locking connection of flange 5 with protective sleeve 2 is able to be implemented. In this way especially durable temperature-resistant sealing of tube 3 with respect to protective sleeve 2 or housing 1 is able to be achieved.

Connection cables 4 are likewise shown schematically in FIG. 1. They include an electrically insulating sheathing 16, preferably made of PTFE, and an electric conductor 7, made of copper or the like, for instance.

Figure 2:
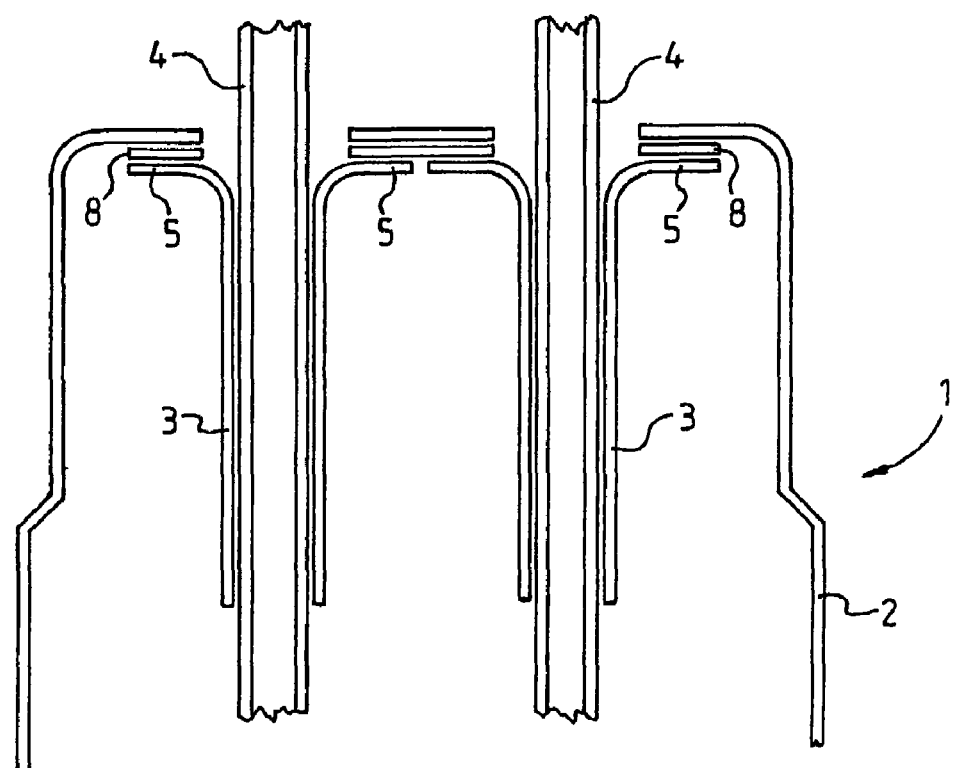
FIG. 2 shows a schematic section through a second sensor unit according to the present invention.

The variant according to FIG. 2 has tubes 3 of a comparable design, which include a flange 5. However, in this variant the sealing between tube 3 and protective sleeve 2 is realized with the aid of a sealing ring 8.

For the purpose of illustration, FIGS. 1 and 2 show the state of the sensor unit prior to sealing or tamping of tubes 3 with connection cables 4. In the completely installed state tubes 3 have a smaller diameter, so that permanent, temperature-resistant sealing between tube 3 and connection cable 4 is realized.

Another variant of the present invention is schematically represented in FIG. 3, tube 3 or tubes 3 having been produced preferably with the aid of flow-drilling methods. Here, as additional exceptional feature, housing 1 or protective sleeve 2 encloses tubes 3. This means that protective sleeve 2 and tubes 3 are formed as one piece.

A fourth variant of the present invention is shown in FIG. 4, a plate 9 being used. Plate 9 had originally been a planar plate 9, and tubes 3 were formed with the aid of flow-drilling methods. Using a welding seam 10, plate 9 is welded to the front end of the preferably cylindrical housing 1 or cylindrical protective sleeve 2.

According to a fifth variant in FIG. 5, a separate tube 3 is used and housing 1 or protective sleeve 2 has a sealing edge 11 or cutting edge 11 into which tube 3 is able to be inserted with an essentially precise fit. A welding spot 12 may be provided to fixate tube 3 on housing 1.

As is illustrated by the different variants according to FIGS. 3 through 5, for example, tube 3 according to the present invention may at least partially be aligned outwardly and/or inwardly, or project beyond housing 1.

The schematically shown plan view according to FIG. 6 shows, for instance, a housing 1 having four tubes 3 to accommodate a total of four connection cables 4. Connection cables 4 are not shown in FIG. 6 for reasons of clarity.

A metallic protective sleeve as well as metallic tubes 3 are preferably used whose connection is ensured by metallic welding. Tube 3 or protective sleeve 3 may be designed in the shape of a cup, for instance, having diameters of 0.01 mm to 6 mm.

In an advantageous manner, tube 3 or metal sleeve 3 is produced by flow drilling methods. If this method is used in the front-end sleeve base, form-locking sealing from tube 3 is already provided.

If flow drilling is used in a circular plate 9 according to FIG. 4, for instance, plate 9 may be sealingly connected to the surrounding tube 2 by a circumferential welding seam.

If individual small metal sleeves 3 according to FIG. 5 are utilized, the sealing from surrounding protective sleeve 2 may be realized by a simple cutting and sealing edge 11 and the connection be limited to one laser welding spot for each small metal sleeve 3.

The illustrated variants of an embodiment basically have the advantage over the related art that the air space within protective sleeve 2 is enlarged and the heat insulation in the sealing region is increased as a result. This leads to a considerably higher temperature resistance in the sealing region of the cable harness.

For instance, holes are introduced in the front-end base of deep-drawn protective sleeve 2 by flow drilling according to FIG. 3, and tubes 3 are formed at the same time. One stranded wire 4 or connection cable 4 is inserted into each of these tubes 3. Tubes 3 are caulked onto PTFE sheathing 16 of stranded wire 4 or connection cable 4. In this way the cable exit of stranded wire 4 out of protective sleeve 2 is sealed.

What is claimed is:

1. A sensor unit for determining a physical sensor parameter of a measuring gas, comprising:
   a sensor housing; and
   at least one connection cable including an electrically insulating cable sheathing and for transmitting at least one of energy and the sensor parameter, wherein:
   the sensor housing includes at least one cable opening for the at least one connection cable,
   the sensor housing includes at least one sealing element for sheathing and sealing the at least one connection cable,
   the at least one sealing element is at least partially formed as a tube,
   the sensor housing is welded to the tube by at least one of at least one welding spot and a welding seam, and
   the tube is coated by electric insulation on the inside.

2. The sensor unit as recited in claim 1, wherein a wall thickness of the tube is several times smaller than the outer diameter of the at least one connection cable.

3. The sensor unit as recited in claim 1, wherein a wall thickness of the tube is approximately between 0.01 mm and 1.0 mm.

4. The sensor unit as recited in claim 1, wherein an outer diameter of the tube is approximately between 0.01 mm and 6.0 mm.

5. The sensor unit as recited in claim 1, wherein, at least in the installed state, an inside diameter of the tube is smaller than an outer diameter of the at least one connection cable in a non-installed state.

6. The sensor unit as recited in claim 1, wherein the tube situated around the at least one connection cable is tamped.

7. The sensor unit as recited in claim 1, wherein the tube includes at least one flange for placement on the sensor housing.

8. The sensor unit as recited in claim 1, wherein the sensor housing encloses the tube.

9. The sensor unit as recited in claim 1, wherein the tube is able to be produced by a flow-drilling operation.

10. The sensor unit as recited in claim 1, wherein the electrically insulating cable sheathing of the at least one connection cable includes polytetrafluorethylene.

11. The sensor unit as recited in claim 1, wherein the at least one connection cable includes at least two connection cables, and at least one tube is assigned to each connection cable.

12. The sensor unit as recited in claim 1, wherein the sensor unit is for determining an oxygen concentration in an exhaust gas of an internal combustion engine.

13. The sensor unit as recited in claim 1, further comprising:
   a sealing ring for sealing between the sensor housing and the tube.

14. The sensor unit as recited in claim 1, wherein the tube is formed from a planar plate.

15. The sensor unit as recited in claim 1, wherein the at least one cable opening includes a cutting and sealing edge for sealing the cable opening from the tube.

* * * * *